United States Patent
Enssle et al.

(10) Patent No.: US 6,210,661 B1
(45) Date of Patent: *Apr. 3, 2001

(54) IL-4 RECEPTOR FOR THE THERAPY, PROPHYLAXIS AND DIAGNOSIS OF ALLERGIC, VIRAL, AND BACTERIAL DISEASES AND OF FUNGAL INFECTIONS

(75) Inventors: Karlheinz Enssle, Marburg-Michelbach; Roland Kurrle, Niederweimar; Leander Lauffer, Gladenbach; Friedrich-Robert Seiler, Marburg, all of (DE)

(73) Assignee: Aventis Pharma Deutschland GmbH, Franfurt am Main (DE)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/692,446

(22) Filed: Aug. 5, 1996

Related U.S. Application Data

(63) Continuation of application No. 08/402,562, filed on Mar. 13, 1995, now abandoned, which is a continuation of application No. 08/112,379, filed on Aug. 27, 1993, now abandoned.

(30) Foreign Application Priority Data

Mar. 13, 1992 (DE) ................................. 42 28 941
Jul. 5, 1993 (DE) ................................. 43 22 330

(51) Int. Cl.[7] .................. A61K 45/00; G01N 33/53; C07K 1/00; C07K 14/00
(52) U.S. Cl. .............. 424/85.2; 424/85.1; 424/184.1; 424/192.1; 435/7.1; 435/7.2; 435/69.1; 435/69.5; 530/350; 530/351
(58) Field of Search .................. 424/85.2, 85.1, 424/184.1, 192.1; 530/350, 351; 435/7.2, 7.1, 69.5, 69.1

(56) References Cited

U.S. PATENT DOCUMENTS

| 5,591,825 | * | 1/1997 | McKnight et al. | 530/350 |
| 5,599,905 | * | 2/1997 | Mosley et al. | 530/350 |
| 5,639,597 | | 6/1997 | Lauffer et al. | |
| 5,658,744 | * | 8/1997 | Ochoa et al. | 435/7.24 |

FOREIGN PATENT DOCUMENTS

| 2045869 | 12/1991 | (CA). |
| 1339207 | 8/1997 | (CA). |
| 0 330 977 A2 | 9/1989 | (EP). |
| 0 367 566 | 5/1990 | (EP). |
| 0 419 091 A1 | 3/1991 | (EP). |
| 0 464 533 A1 | 1/1992 | (EP). |
| 0 488 170 A1 | 6/1992 | (EP). |
| WO 90/05183 | 5/1990 | (WO). |
| 9101004 | * 1/1991 | (WO). |
| WO 92/05698 | 4/1992 | (WO). |

OTHER PUBLICATIONS

Manual of Clinical Microbiology, 2nd Edition, Lennette et al, editors, pp. 550–556, 611–616, Jan. 1, 1974.*
Textbook of Medicine, 15th Edition, Beeson et al, editors, pp. 546–547, 630–631, 583–587, Jan. 1, 1979.*
Ogata, M. et al., PNAS, 86:4215–4219, Jun. 1989.*
Maher, DW. et al, Prog Growth Factor Res., 3(1):43–56, 1991.*
Scott, Phillip, J. Immunol, 147(9):3149–3155, Nov. 1, 1991.*
Del Prete, C et al, Allergie et Immunologie, 23(6):239–243, 1991.*
Luigina Romani et al., "Neutralizing Antibody to Interleukin 4 Induces Systemic Protection and T Helper Type 1–associated Immunity in Murine Candidiasis", J. Exp. Med., vol. 176, pp. 19–25, Jul. 1992.
Luigina Romani et al., "Th1 and Th2 Cytokine Secretion Patterns in Murine Candidiasis: Association of Th1 Responses with Acquired Resistance", Infection and Immunity, vol. 59, No. 12, pp. 4647–4654, Dec. 1991.
Michael Sadick et al., "Cure of Murine Leishmaniasis with Anti–Interleukin 4 Monoclonal Antibody", J. Exp. Med., vol. 171, pp. 115–127, Jan. 1990.
René Chatelain et al., "IL–4 Induces A Th2 Response in Leishmania major–Infected Mice", The Journal of Immunology, vol. 148, No. 4, pp. 1182–1187, Feb. 15, 1992.
Fred Finkelman et al., "Regulation of Murine in vivo IgG and IgE Responses by a Monoclonal anti–IL–4 Receptor Antibody", International Immunology, vol. 3, No. 6, pp. 599–607, 1991.
A. Sher et al., "Regulation of Immunity to Parasites by T Cells and T Cell–Derived Cytokines", Annu. Rev. Immunol., 10:385–409, 1992.
H. Renz et al., "Inhibition of Allergen–Induced And Allergen–Specific IgE and IgG1 Production By Soluble IL–4 Receptor (sIL–4R)," The Journal of Allergy And Clinical Immunology, vol. 91, No. 1(2) (Jan. 1993) p. 234.
W. Fanslow et al., "Soluble Forms Of CD40 Inhibit Biologic Responses Of Human B Cells," The Journal of Immunology, vol. 149, No. 2 (Jul. 15, 1992) pp. 655–650.
"Diversity of Cytokine Synthesis and Function of Mouse CD4+T Cells", Mosmann et al., Immunological Reviews, 123:209–229 (1991).
"Human TH1 and TH2 subsets: doubt no more", Sergio Romagnani, Immunology Today, 12(8):256–257 (1991).

(List continued on next page.)

Primary Examiner—Rodney P. Swartz
(74) Attorney, Agent, or Firm—Finnegan, Henderson, Farabow, Garrett & Dunner, L.L.P.

(57) ABSTRACT

The IL-4 receptor for the therapy, prophylaxis and diagnosis of allergic, viral, parasitic and bacterial diseases and of fungal infections. The invention relates to the il-4 receptor or variants thereof for the therapy, prophylaxis and diagnosis of allergic, viral, parasitic and bacterial diseases and of fungal infections.

15 Claims, No Drawings

OTHER PUBLICATIONS

"Helper T–cell Subsets in Mouse Trichuriasis", Else and Grencis, Parasitology Today 7(11):313–316 (1991).

"Parasites and Human T–cell Subsets", Parasitology Today, 7(10):261 (1991).

"Functional subsets of allergen–reactive human CD4+ T cells", Kapsenberg et al., Immunology Today 12(11):392–395 (1991).

"Human Interleukin 4 Receptor Confers Biological Responsiveness and Defines A Novel Receptor Superfamily", Idzerda et al., J. Exp. Med. 171:861–873 (1990).

"Cytokine Receptors and B Cell Functions I. Recombinant Soluble Receptors Specifically Inhibit IL–1– and IL–4–Induced B Cell Activities In Vitro", Maliszewski et al., The Journal of Immunology 144:3028–3033 (1990).

"Retention of Ligand Binding Activity By the Extracellular Domain of The IL–1 Receptor", Dower et al., The Journal of Immunology, 142:4312–4320 (1989).

"The Murine Interleukin–4 Receptor: Molecular Cloning and Characterization of Secreted and Membrane Bound Forms", Mosley et al., Cell 59:335–348 (1989).

"Expression and Characterization of Human CD4: Immunoglobulin Fusion Proteins", Zettlemeissl et al., DNA and Cell Biology 9(5):347–353 (1990).

Knutsen et al., "Asp f1 CD4+ $T_{h2}$–like T–cell Lines in Allergic Bronchopulmonary Asperigillosis", J. Allergy Clin. Immunol., 94(2):215–221 (1994).

Clerici et al., "A $T_h1 \rightarrow T_2 2$ Switch is a Critical Step in the Etiology of HIV Infection", Immunology Today, 14(3):107–111 (1993).

Robinson et al., "Predominant $T_{H2}$–like Bronchoalveolar T–lymphocyte Population In Atopic Asthma", New England J. of Medicine, 326(5):298–304 (1992).

Ying et al., "T Lymphocytes and Mast Cells Express Messenger RNA for Interleukin–4 in the Nasal Mucosa in Allergen–induced Rhinitis", Immunology, 82:200–206 (1994).

Maggi et al., "Accumulation of Th–2–Like Helper T Cells in the Conjunctiva of Patients with Vernal Conjunctivitis", J. Immunology, 146(4):1169–1174 (1991).

Robinson et al., "Activation of CD4+ T cells, increased $T_{H2}$–type Cytokine mRNA Expression, and Eosinophil Recruitment in Bronchoalveolar Lavage After Allergen Inhalation Challenge in Patients With Atopic Asthma", J. Allergy Clin. Immunol., 92(2):313–324 (1993).

van Reijsen et al., "Skin–derived Aeroallergen–specific T–cell Clones of Th2 Phenotype in Patients With Atopic Dermatitis", J. Allergy Clin. Immunol., 90(2):184–193 (1992).

Millner et al., Abstract of "Soluble IL–4R (sIL–4R) Down Regulates Allergen Specific Lymphocyte Functions in Most Severe Atopic Dermatitis", American Academy of Allergy and Immunology, Abstract Serial No. 13815 (1994).

Renz et al., Abstract of "Aerosolized Soluble IL–4R (sIL–4R) Prevents Development of Immediate Hypersensitivity Responses in the Mouse", Experimental Biology 94 (1993).

Enssle et al., "Regulation of Interkeukin–4 Activity by Soluble Interleukin–4 Receptors", J. Clin. Lab. Analysis, 9:450–455 (1995).

Enders et al., Abstract of "Recombinant Soluble Interleukin–4 Receptor Inhibits Allergen Induced Murine Asthma Bronchiale", 9th Int. Congress of Immunology (1995).

Gessner et al., "Recombinant Soluble Interkeukin–4 (IL–4) Receptor Acts as an Antagonist of IL–4 in Murine Cutaneous Leishmaniasis", Infection and Immunity, 62(10):4112–4117 (1994).

Puccetti et al. "Cure of Murine Candidiasis by Recombinant Soluble Interleukin–4 Receptor", J. Infectious Diseases, 169:1325–1331 (1994).

Schorlemmer et al., "Immunoregulation by Recombinant Interkeukin–4 Receptor (IL–4–R) of Murine GvH and SLE–like diseases in BDF1 Hybrid Mice and MRL/lpr Autoimmune Mice", Agents Actions 41:C180–C182 (1994).

Schorlemmer et al., "Modulation of the Immunoglobulin Dysregulation in GvH– and SLE–like Diseases by the Murine IL–4 Receptor (IL–4–R)", Inflamm. Res. 44(2):S194–S196 (1995).

Kung et al., "Characterization of a Murine Model of Allergic Pulmonary Inflammation", Int. Arch. Allergy Immunol., 105:83–90 (1994).

* cited by examiner

IL-4 RECEPTOR FOR THE THERAPY, PROPHYLAXIS AND DIAGNOSIS OF ALLERGIC, VIRAL, AND BACTERIAL DISEASES AND OF FUNGAL INFECTIONS

This is a continuation of application Ser. No. 08/402,562, filed Mar. 13, 1995, now abandoned, which is a continuation of Ser. No. 08/112,379, filed Aug. 27, 1993, now abandoned.

The therapy and prophylaxis of many allergic, viral, parasitic and bacterial diseases remain a serious problem. The invention relates to the use of the IL-4 receptor or of derivatives thereof for the therapy, prophylaxis and diagnosis of such diseases.

It is known that in the course of some parasitic, viral and bacterial diseases there are changes in subpopulations of lymphocytic and monocytic cells. This relates, for example, to the increased occurrence of so-called T-helper cells of type 2 (called TH2 cells hereinafter). T cells can in general be divided into subpopulations on the basis of surface markers and on the basis of their function. Thus, for example, T-helper lymphocytes carry CD4 surface molecules and, after their activation, secrete cytokines.

Analyses of the cytokine pattern of cloned T-helper cells from healthy mice or mice stimulated with allogeneic cells revealed that these cells produce interleukin-2, interleukin-4, gamma-interferon, interleukin-5, interleukin-6, interleukin-10 and lymphotoxin (T-helper cells of the so-called THO type).

After stimulation of mice, for example with the bacterial antigen Brucella abortus or with Mycobacterium tuberculosis, the clones found in particular after cloning of T-helper cells secrete lymphotoxin, gamma-interferon and interleukin-2, but little or no interleukin-4, interleukin-5, interleukin-6 and interleukin-10 (T-helper cells of the so-called TH1 type).

After infection of, for example, susceptible mice with parasitic pathogens such as Leishmania major, the clones particularly occurring on clonings of T-helper cells produce increased amounts of interleukin-4, interleukin-5 and interleukin-10 but reduced or undetectable amounts of interleukin-2 and gamma-interferon (T-helper cells of the TH2 type) (Mosmann et al., Immunological Reviews 1991, No. 123, 209–229; S. Romagnani, Immunology Today, 256–257, Vol. 12, No. 8 1991).

This increased occurrence of TH2 lymphocytes has already been detected in some infectious diseases in animals and in humans (Else and Grencis, Parasitology Today, Vol. 7, No. 11, 1991, pp. 313–316; Parasitology Today, Vol. 7, No. 10, 1991, p. 261) and is also reflected in secondary parameters. Thus, mice infected with Leishmania major in general showed a reduced production of gamma-interferon, a large increase in serum IgE and eosinophilia.

In humans with, for example, lepromatous leprosy, leishmaniasis and schistosomiasis and infections with Mycobacterium tuberculosis, the IgE concentration in the serum of these patients was generally found to be much higher than in the sera of normal subjects. In parasitic infections, an eosinophilia is often observed during the course of the disease.

IgE-mediated allergic reactions of the immediate type as well as atopic dermatitis and asthma are also characterized by a dysregulation of this type. For example, antigen-specific T-cell clones from skin biopsies from patients with atopic dermatitis are especially of the TH2 type (Kapsenberg et al., Immunology Today, Vol. 12, No. 11, 1991, 392–395).

It has now been found that diseases which are characterized by an increased occurrence of T-helper cells of the TH2 type can be diagnosed and treated therapeutically and/or prophylactically with the aid of IL-4R or of derivatives thereof.

The invention therefore relates to the use of the IL-4 receptor or of derivatives thereof for the production of a pharmaceutical for the therapy and/or prophylaxis or for producing a diagnostic aid for identifying diseases in which there is increased occurrence of T-helper cells of the TH2 type.

"Derivatives" of IL-4R mean for the purpose of the invention functionally equivalent parts, mutants or variants of IL-4R, especially the extracellular part of IL-4R, in particular from amino acid 1 to about 209 of the mature protein of the human IL-4 receptor as well as glycosylation mutants thereof. It is also possible to employ fusion proteins which contain IL-4R or derivatives thereof as well as other proteins or parts of proteins, preferably the Fc portion of antibodies (IL-4R/Fc fusion protein), for the use of the receptor according to the invention. It is furthermore possible to employ IL-4R, derivatives or fusion proteins thereof in combination products for the diagnosis, therapy and/or prophylactic treatment of the said diseases, preferably in combination with gamma-interferon.

Also advantageous is therapy in combination with purified allergens or portions thereof, especially a desensitization in combination with purified allergen in patients with, for example, allergic rhinitis for specific immunotherapy (desensitization).

Also advantageous is therapy in combination with gamma-interferon and/or substances which block the interaction of the cellular surface molecule CD40 with its ligand, the cellular surface molecule CD40 ligand, preferably a soluble variant of the CD40 surface molecule itself such as, for example, a CD40/Ig fusion protein corresponding to the description hereinafter or derivatives thereof.

"Derivatives" of a soluble variant of the CD40 surface molecule mean for the purpose of the invention those functionally equivalent parts or variants which block the interaction of the cellular CD40 with the cellular surface molecule CD40 ligand.

The diseases include allergies and infections, especially viral, bacterial and parasitic infections, as well as fungal infections; preferably infections with the human immunodeficiency virus (HIV), mycobacteria, especially Mycobacterium leprae, with listeria, with protozoa, especially of the genera Leishmania and Plasmodium, with helminths, especially of the genera Schistosoma, Nippostrongylus and Heligmosomoides with Trichurida, Trichinella, Taenia (Cysticercus), Candida and Aspergillus. However, it is also possible to diagnose, treat or prophylactically treat allergic reactions of the immediate type, especially IgE-mediated reactions. These include, in particular, atopic dermatitis and asthma.

The administration forms are generally different for different diseases. Thus, for example, topical administration may be advantageous for some diseases. Advantageous examples are administration by inhalation for asthma, administration in eyedrops for conjunctivitis, and dermal or intradermal administration for atopic dermatitis, because the pathological TH2 cells can be detected in particular topically.

It has been reported that the human IL-4 receptor is composed of a total of 825 amino acids (Idzerda, R. J. et al. (1990) J. Exp. Med. 171, 861–873). According to Idzerda et al., the 25 N-terminal amino acids function as signal peptide, and the mature human IL-4 receptor is composed of 800 amino acids and has a three-domain structure comprising 1.

extracellular domain (207 amino acids), 2. transmembrane region (about 24 amino acids), 3. cytoplasmic domain (569 amino acids). Preparation of the IL-4 receptor by genetic engineering is particularly advantageous because this makes it possible to prepare directly the amounts of substance required for therapy.

IL-4R can be prepared, for example, as described in International Patent Application WO90/05183. According to this, a cDNA gene bank was produced, for example, from the T cell line T22 and screened with a probe for IL-4R-specific DNAs. It is possible to use as probe the hybrid-subtracted cDNA of a mouse cell line described in WO90/05183. However, it is also possible to use an IL-4R-specific hybridization probe, for example one or more probes about 20 nucleotide long, for example from position 193–210, for screening the cDNA bank. After positive clones have been checked for IL-4R-specific cDNA, for example by sequencing, the IL-4R DNA which has been found can be cloned into suitable expression vectors, for example pCAV/NOT (WO90/05183), and be expressed completely or in portions in suitable host cells, for example COS-7, BHK-21 or CHO cells. If only the cDNA portion which codes for the extracellular region of the IL-4 receptor is used for expression, the extracellular region of the interleukin-4 receptor is generally secreted by transfected cells into the culture medium. For this purpose, the cDNA is altered by genetic engineering methods corresponding to the state of the art in such a way that a stop codon is introduced after the coding sequence for the extracellular region of a receptor, or desired portions thereof, and the cDNA altered in this way is cloned into suitable expression vectors (Maliszewski et al. (1990), J. Immunol. 144, 3028–3033; Dower et al. (1989), J. Immunol. 142, 4314). In many cases, for example in that of the murine IL-4 receptor, the isolated cDNAs code for a naturally occurring secreted form of the receptor (Mosley et al. (1989), Cell 59, 335). These cDNAs can then be used directly for the preparation of expression vectors. The secreted proteins can be purified from the culture medium for example by ligand affinity chromatography or immunoaffinity chromatography using specific monoclonal antibodies (Maliszewski et al. (1990), J. Immunol. 144, 3028–3033). It is furthermore possible, as described in European Patent Application EP-A1-0 464 533, by genetic engineering means to prepare, and bring about the expression of, fusion proteins between IL-4R or derivatives thereof with other proteins, for example with immunoglobulin portions, for example the Fc portion of antibody molecules (called IL-4R/Fc hereinafter). The advantage of such fusion proteins is that the half-life is extended and enrichment and purification via protein A-Sepharose affinity chromatography are simplified.

The problem-free purification by affinity chromatography and the possibly improved pharmacokinetic properties mean that the synthesis of soluble forms of the IL-4 receptor as immunoglobulin fusion protein is particularly advantageous.

CD40 is a type I membrane protein, i.e. it is composed of an (amino-terminal) extracellular region, of a transmembrane region and of a (carboxy-terminal) cytoplasmic region. cDNA coding for CD40 can be isolated, for example, from a cDNA bank of Raji cells using the panning method (Stamenkovic, I. et al. (1989) EMBO J., Vol. 8, pp. 1403–1410). Various options which are well known to the skilled worker exist for bringing about the expression of the protein, which is normally membrane-associated, as soluble form. For example, it is possible in a polymerase chain reaction using mutagenizing primers to introduce a stop codon at the end of the cDNA sequence coding for the extracellular region. The cDNA altered in this way then codes for a CD40 protein which, because of the absence of the membrane anchor, is secreted like other secretary proteins by the cell (Fanslow, W. C. et al. (1992) J. Immunol., pp. 655–660). It may also be advantageous to use soluble recombinant immunoglobulin fusion proteins, whose preparation is described by way of example in EP-A-0 464 533. In particular, CD40/Ig fusion proteins are also disclosed in the literature (Fanslow et al. (1992) J. Immunol., Vol. 149, pp. 655–660 and Noelle et al. (1992) Proc. Natl. Acad. Sci USA, Vol. 89, pp. 6550–6554). Both publications describe CD40/Ig fusion proteins composed of the extracellular region of CD40 fused to hinge, CH2 and CH3 domains of the heavy chain of a human immunoglobulin G1 molecule. To prepare the corresponding DNA constructs, suitable restriction cleavage sites were introduced into the CD40 cDNA by means of the polymerase chain reaction using mutagenizing primers (Fanslow et al., (1992) J. Immunol., Vol. 149, pp. 655–660) or naturally occurring restriction cleavage sites in the CD40 cDNA were utilized (Noelle et al., (1992) Proc. Natl. Acad. Sci USA, Vol. 89, pp. 6550–6554).

Soluble forms of CD40 can be expressed in known prokaryotic or eukaryotic systems, but preferably in mammalian cell cultures, as recombinant proteins and be purified from culture supernatants or cell digests by conventional methods. Apart from a possible direct therapeutic use of the soluble CD40 molecules, the latter can furthermore also be employed for the identification of other substances which block the interaction of membrane-associated CD40 and CD40 ligands and thus likewise have therapeutic potential. This can take place, for example, in cell-free receptor binding assays (EP-A-0 488 170) in which the soluble CD40 molecules are present on a solid phase, and the binding of soluble CD40 ligands is followed by means of suitable labeling or antibodies. Assays of this type provide, because of the possibility of automating them, the means for investigating a large number of substances for their interaction with CD40/CD40 ligands (receptor screening).

Used for the examples detailed hereinafter were the, as defined by Idzerda et al. (1990, J. Exp. Med. 171, 861–873) and Maliszewski et al. (1990, J. Immunol. 144, 3028–3033), extracellular regions and naturally occurring soluble forms of human and murine IL-4 receptor (called huIL-4R and muIL-4R respectively hereinafter) which, after double selection with methotrexate and G418 (EP-A 0330 977), were secreted by stably expressing BHK cells as soluble protein into the culture medium and purified by immunoaffinity chromatography. Also used were receptor/immunoglobulin fusion proteins (EP-Al-0 464 533) which are composed of the extracellular region of human or murine IL-4 receptor with hinge, CH2 and CH3 domains of a human IgG1 or murine IgG2b molecule (Zettlmeißl et al. (1990) DNA and Cell Biol. 9, 347–353) (called huIL-4R/Fc and muIL-4R/Fc respectively hereinafter) and, likewise after expression in BHK cells, were purified by protein A-Sepharose affinity chromatography.

IL-4R and IL-4R/Fc are equally effective at neutralizing in a bioassay the interleukin-4 of the homologous species in each case (Example 1). It was furthermore possible to detect inhibition of human T-cell clones of the TH2 type by huIL-4R/Fc also in vitro. The IL-4 formed by these clones in vitro was neutralized by huIL-4R/Fc. This resulted in a reduction in proliferation. The growth of control clones of the TH1 type was unaffected by huIL-4R/Fc (Example 4).

It was additionally found that huIL-4R/Fc is able to suppress in vitro the synthesis which is induced by IL-4

(Example 2), and surprisingly also the antigen-specific (Example 3) synthesis, of IgE by human peripheral blood mononuclear cells. Surprisingly, there is a therapeutic or prophylactic effect on infections and disorders of the immune system, as it has been possible to demonstrate by way of example for the murine soluble interleukin-4 receptor in an animal model of murine listeriosis, in an animal model (mouse) of Cysticercus crassiceps infection, an animal model for systemic lupus erythematosus (MRL/1 mouse), an animal model (mouse) of chronic graft-versus-host reaction and in an animal model (mouse) for allergen-induced asthma (Example 5).

EXAMPLE 1

Biological activity of the human and murine variants of IL-4R and IL-4R/Fc;

The biological activity was measured in a bioassay. IL-4 binds strictly species-specifically to the IL-4 receptor. For this reason, a cell line which is of murine origin and in which the murine IL-4 receptor is membrane-associated was used. This cell line was transfected with the complete gene for human interleukin-4 receptor. Murine and human membrane-associated receptors are functionally expressed simultaneously by this cell line, and proliferation of the cell line depends both on murine and on human IL-4 (Mosley et al., Cell, Vol. 59, 335–348, Oct. 20, 1989).

Murine IL-4 was used to detect muIL-4R and muIL-4R/Fc (Table 1). Proliferation of the cell line depends on murine IL-4 (Table 1). Constant use of interleukin-4 and simultaneous addition of muIL-4R or muIL-4R/Fc results in a concentration-dependent neutralization of interleukin-4. Since less interleukin-4 is available for the cell line, proliferation diminishes. A control protein with the same Fc portion does not show this effect. Differences between muIL-4R and muIL-4R/Fc in the concentration-dependent inhibition in Table 1 are attributable to the different molecular weights.

Table 2 shows the bioactivity of human interleukin-4 and, corresponding to Table 1, the specific neutralizing effect of huIL-4R and huIL-4R/Fc. Differences between huIL-4R and huIL-4R/Fc in the concentration-dependent inhibition are attributable to the different molecular weights.

EXAMPLE 2

Suppression of IL-4-induced IgE synthesis by huIL-4R/Fc

Human peripheral blood mononuclear cells were isolated and cultivated in Iscove's culture medium containing 5% FCS at a cell count of $1\times10^6$ cells with 1 ml culture volume per culture well in 24-well plates for 48 hours. 300 ng/ml human interleukin-4 were added to the medium. Membrane-bound IgE which was already present was released into the culture medium during this prestimulation. After the 48 hours, the cells were washed to remove released IgE. The cells were subsequently cultivated in Iscove's culture medium containing 5% FCS at a cell concentration of $1\times10^5$ cells in 200 µl culture volume in 96-well flat-bottomed culture plates. 0 ng/ml, 3 ng/ml and 30 ng/ml interleukin-4 were added to the medium. The batch was carried out without further addition or addition of, in each case, 3 µg/ml huIL-4R/Fc or huCD4/Fc. huCD4/Fc acted as control for the Fc portion of IL-4R/Fc and was prepared as described in EP-A2-0 325 262. The Fc portions of huCD4/Fc and huIL-4R/Fc are identical (IgG1). After a culture time of 10 days, the culture medium was removed and assayed in an ELISA for human IgE. Table 3 shows the result of this test. The IL-4-induced IgE synthesis was specifically suppressed by addition of huIL-4R/Fc.

EXAMPLE 3

Human peripheral blood mononuclear cells were isolated. 5000 cells per well in a 96-well culture plate were cultivated with 200 µl of Iscove's culture medium containing 10% FCS for 14 days. At the start of the culture, no further addition was made, or 100 SQ units (as stated by the manufacturer) of purified mite antigen (Derm. Pt., Order No. Sq 503, from Scherax, Hamburg) alone or mite antigen and 3 µg/ml huIL-4R/Fc were added. A mixture with mite antigen and 3 µg/ml TW1 acted as Fc control. TW1 is a human monoclonal antibody which has specificity for rabies antigen and which has the same isotype as huIL-4R/Fc. TW1 was prepared as described in EP-0 445 625 A1. After this, supernatant was removed and assayed for human IgE in an ELISA. It was found that the antigen-induced production of IgE is specifically suppressed by huIL-4R/Fc (Table 4).

EXAMPLE 4

Inhibition of antigen-induced proliferation of T-cell clones of the TH2 subtype

T-cell clones were isolated from the skin of patients with atopic dermatitis. A high proportion of the clones secreted after stimulation in vitro cytokines of the TH2 type, and only a small proportion of clones of the TH1 type was found. The proliferation assays were carried out in 96-well microtiter plates with $1\times10^4$ cloned T cells and $1\times10^5$ irradiated autologous PBL as stimulator cells in Iscove's culture medium containing 4% human AB serum. The culture was carried out with 0.5 µCi/culture well of $^3$H-thymidine in an incubator at 37° C., passing $CO_2$ through, for 18 h. After 18 hours, the proliferation of the cells was determined by means of the incorporated thymidine. For the production of cytokines in the supernatant, $1\times10^6$/ml cloned T cells were stimulated with Iscove, 10% FCS and 10 µg/ml concanavalin A in 24-well culture plates. The supernatants were removed after a culture time of 24 h in an incubator (37° C.) through which $CO_2$ was passed. The culture supernatants were assayed for the content of human interleukin-2 and human interleukin-4 in bioassays. The bioassays are based on cell lines whose proliferation depends on human interleukin-2 and human interleukin-4 respectively (Mosley et al. Cell, Vol. 59, 335–348, Oct. 20, 1989). No IL-2, but a large amount of IL-4 was detectable in the supernatants of one TH2 clone. On addition of 3 µg/ml of huIL-4R/Fc it was now possible to detect only 10 ng/ml IL-4 in place of 49 ng/ml IL-4. Supernatants of a TH1 clone contained a comparatively large amount of IL-2 but only a little IL-4. The interleukin-2 concentration in the supernatants of the TH1 clone is not significantly affected by addition of huIL-4R/Fc during the culture. It was possible to demonstrate in the proliferation experiment that proliferation of the TH2 clone but not of the TH1 clone is suppressed by adding 3 µg/ml huIL-4R/Fc (Table 5). It was further possible to show that the antigen-specific proliferation of mite-specific TH2 clones, but not of TH1 clones, is suppressed by adding huIL-4R/Fc. It was possible to demonstrate in a further experimental approach that the IgE synthesis induced by mite antigen in a mixture of a TH2 clone with autologous B lymphocytes from the same donor can be suppressed by adding huIL-4R/Fc.

EXAMPLE 5

Inhibition of the skin test reaction and other parameters by treatment with muIL-4R after pulmonary allergization of mice Balb/c mice were sensitized to ovalbumin by inhaling an aerosol of a solution of ovalbumin in PBS (500 µg/7 ml). The procedure is described in Renz et al. 1992, J. Allergy Clin. Immunol. 89:112. The aerosol was produced in an ultrasonic atomizer (PulmoSonic Model 25, The De Vilbiss Co., Somerset, Pa.). More than 90% of the generated particles were 1–5 μm in size. The animals were exposed to the ovalbumin-containing aerosol for 20 minutes on each of days 1, 7, 14 and 21. In order to examine the effect of soluble muIL-4R in the model, 150 μg/injection muIL-4R i.p., PBS and 11B11 (rats monoclonal antibody against murine IL-4, Ohara, J. and W. E. Paul, 1985, Nature 315:333) were administered on each of days −2, −1, 1, 2, 7, 8, 14, 15, 21 and 22.

On day 23 of the experiment, a skin test with ovalbumin (OVA) was carried out on each group. The procedure is described in Saloga et al. 1993, J. Clin. Invest. 91:133–140.

The result is summarized in Table 6 and shows a distinct reduction in the number of animals with a positive skin test reaction from 83.3% to 22.2%.

The effect of muIL-4R on OVA-specific IgE and the tracheal constriction of isolated tracheae of these animals was investigated in the same experimental system. The investigation methods are described in Renz, H. et al. 1992, J. Allergy Clin. Immunology, 89:112 and in Larsen et al. 1992, J. Clin. Invest. 89:747. The experiments were carried out with the same ovalbumin and muIL-4R administration scheme and with the same dosage as described above in this example. The results are summarized in Table 7. The tracheal constriction was carried out ex vivo by stimulation in an electric field (data in ES50 units). The IgE concentration was determined from serum in an ELISA (data in relative units based on a murine control serum with a high anti-OVA titer). The sera were taken on day 23 of the experiment. The result shows a distinct normalization of tracheal function from 2.47 to 3.4 ES50 and a reduction in the IgE titer. OVA-specific IgG1 was measured in parallel and is likewise reduced (not detailed). An increase in IgG2a is observed at the same time.

The skin test reaction after pulmonary sensitization with ovalbumin (administration scheme, dosage and method as described above in the same example), and pulmonary treatment with muIL-4R was tested in parallel in the same experimental system as described above. For this experiment, in analogy to the ovalbumin method, 500 μg of muIL-4R in 7 ml of PBS were atomized to an aerosol in an ultrasonic atomizer on each of days −2, −1, 1, 2, 7, 8, 14, 15, 21 and 22. The animals were exposed to the aerosol in a closed container for 20 minutes (4 animals per atomization). It was ensured by preliminary tests that the biological activity of the muIL-4R protein is retained on ultrasonic atomization. It was also established that an animal inhales about 0.5–5% of the total amount of 500 μg of muIL-4R. A skin test was carried out on day 23 of the experiment as described above. The result is shown in Table 8. The effect in the skin test with topical administration, despite the smaller amount of muIL-4R administered per animal (final amount inhaled: 0.5–5% of 125 μg of muIL-4R/animal), is observed to be about the same as with intraperitoneal treatment (150 μg/animal).

EXAMPLE 6
Effect of interleukin-4 receptor on induced chronic graft versus host disease (cGvHD)

cGvHD was induced in female B6D2F1 hybrid animals (parental strains C57Bl/g and DBA/2) weighing 15–18 g by 4 intravenous injections of 1×10$^8$ spleen cells from DBA/2 mice per injection in 4 consecutive weeks. The proteinuria which developed was monitored with the N-Combur test (Boehringer Mannheim GmbH, Mannheim, Germany). 10 animals were employed per group. One group received 2 mg/kg murine interleukin-4 receptor (muIL-4R/Fc) on each of days 27, 28, 29, 30 and 31, another group was treated with the same dosage and the same administration scheme with human interleukin-4 receptor (huIL-4R/Fc) as control protein, and one control group was treated with PBS. Table 9 shows the surviving animals as fractions of the animals in the groups, and Table 10 shows the changes in the average protein levels in the urine of the animals in the various groups. A significant effect of muIL-4R is to be seen both in the numbers of survivors and in the proteinuria. Another experiment was carried out with induction of cGvHD as described above. The division of the groups was the same but the treatment was carried out after the appearance of glomerulonephritis on days 63, 64, 65, 66 and 67, that is to say therapeutically (intravenously 2 mg/kg huIL-4R/Fc or muIL-4R/Fc on each of these days). The fractions of surviving animals and the protein levels in the urine of the animals are shown in Tables 11 and 12 respectively. In another experiment with the same induction of the cGvHD and the same division of the groups, monomeric muIL-4R or monomeric huIL-4R was administered intravenously with 2 mg/kg per injection five times every third day starting on day 24. Once again, similar to the previous experiments in this example, a significant suppression of the parameters of cGvHD and an increase in the survival rate of the animals in the group treated with muIL-4R were observed. In this experiment, blood was taken from the animals during the experiment. Murine immunoglobulin E (IgE) in these sera was determined in an ELISA. This IgE concentration increases during the disease and falls again after the measurement on day 59 in the experiment described. On treatment with muIL-4R, this fall starts at an earlier time, after the measurement on day 45. Table 13 shows the changes in the average IgE concentration of 3 animals selected at random from the group treated with muIL-4R and the control group (treatment with PBS).

EXAMPLE 7
Treatment of a spontaneous autoimmune disease in MRL/1 mice similar to human systemic lupus erythematosus MRL/Mp-Lpr-Lpr (MRL/1) mice about 12 weeks old were treated intravenously (i.v.) on each of 5 consecutive days with buffer control (PBS), murine interleukin-4 receptor-Fc fusion protein (muIL-4R/Fc) or human interleukin-4 receptor-Fc fusion protein (huIL-4R/Fc) as control protein. The animals were sacrificed in week 25. Spleens, lymph nodes and blood were removed. The weights of the spleens and lymph nodes were determined and various parameters from blood or serum were determined. Antibodies against double-stranded DNA (dsDNA) and rheumatoid factor (RF) were determined in ELISA as described in Schorlemmer et al. (Int. J. Immunotherapy 7:169, 1991). The change in the survival rates is shown in Table 14, and the other parameters in week 25 are shown in Table 15. A distinct effect of muIL-4R/Fc on the disease is evident both from the change in the numbers of surviving animals and from the other parameters in week 25.

EXAMPLE 8
Treatment of an infection with Cysticercus (Taenia) crassiceps in the mouse with murine interleukin-4 receptor For the experiment, on day 0, NMRI mice with body weights of 15–25 g were infected with 5 individual metacestodes of the Cysticercus (Taenia) crassiceps strain MR-1 i.p. in 1 ml of PBS per mouse. 10 animals were employed per experimental group. One control group was not infected (injection of PBS without metacestodes). One group was infected but not treated. One group was infected and treated i.p. with 100 μg of muIL-4R on each of days −1, 0, 1, 7, 14, 20, 30, 35, 40, 45, 50, 55 and 63. Another group was infected and treated with huIL-4R as control protein in analogy to the treatment with muIL-4R. On day 76, the animals were weighed and dissected. The animals in which it was possible to find metacestodes in the abdominal cavity were determined. The wet weight of the metacestodes found in each animal was determined for the positive animals. A distinct reduction in the total weight of the metacestodes was found in the group treated with murine interleukin-4 receptor (Table 16).

EXAMPLE 9
Effect of muIL-4R on murine *Candida albicans* infection

Female hybrid mice (BALB/cCrxDBA/2Cr)F1 (CD2F1) were infected with the highly pathogenic *Candida albicans* strain CA-6 ($5\times10^4$ cells intravenously) (day 0 of the test). Starting 24 hours before the infection, the animals received 100 µg of muIL-4R in 250 µl of PBS intraperitoneally once on day −1, twice on each of days 0 and 1 and once on each of days 2 and 3. Control animals received alternatively, using the same scheme, purified mouse serum albumin (MSA), huIL-4R or PBS. All the animals treated with mouse serum albumin (16 animals), huIL-4R (16 animals) and PBS (24 animals) developed a progressive Candida infection with average survival times of 14–17 days after infection. 91.6% of the animals treated with muIL-4R (24 animals) survived. These surviving animals were reinfected with *Candida albicans* ($10^6$ cells) 8 weeks after infection. All the animals survived this reinfection. In normal, untreated animals, this infection dose leads to a lethal infection with survival times of 2–3 days after infection.

TABLE 1

Bioactivity of murine IL-4 receptors
Standard plot for murine IL-4

| ng/ml | CPM | S.D. |
|---|---|---|
| 100 | 46609 | 7.4 |
| 20 | 47809 | 8.1 |
| 0.4 | 43550 | 11.1 |
| 0.8 | 25534 | 7.9 |
| 0.16 | 8456 | 13.7 |
| 0.032 | 1987 | 10.7 |
| 0.064 | 901 | 12.4 |

1 ng/ml murine IL-4 constant

| | Mu IL-4R | | Mu IL-4R/Fc | | Fc control | |
|---|---|---|---|---|---|---|
| µg/ml | CPM | S.D. | CPM | S.D. | CPM | S.D. |
| 10 | 635 | 7.7 | 3844 | 35.7 | 34696 | 15.1 |
| 1 | 1285 | 17.1 | 3482 | 11.6 | 38452 | 6.0 |
| 0.1 | 7417 | 10.9 | 14408 | 6.2 | 39532 | 8.9 |
| 0.01 | 27038 | 2.3 | 32310 | 14.9 | 35308 | 3.1 |
| 0.001 | 33187 | 7.7 | 34658 | 7.5 | 39290 | 5.4 |
| 0.0001 | 31881 | 4.5 | 36931 | 14.1 | 38388 | 4.1 |
| 0.00001 | 36059 | 5.2 | 36719 | 5.3 | 40911 | 6.4 |
| 0.0 | 34112 | 5.5 | 37417 | 4.1 | 37663 | 14.5 |

(Standard deviation in %)

TABLE 2

Bioactivity of human IL-4 receptors
Standard plot for human IL-4

| ng/ml | CPM | S.D. |
|---|---|---|
| 100 | 134112 | 4.0 |
| 20 | 125877 | 3.0 |
| 4 | 127607 | 8.6 |
| 0.8 | 91743 | 4.7 |
| 0.16 | 45908 | 9.2 |
| 0.032 | 20898 | 3.9 |
| 0.064 | 12385 | 7.1 |

1 ng/ml human IL-4 constant

| | Hu IL-4R | | Hu IL-4R/Fc | | Fc control | |
|---|---|---|---|---|---|---|
| µg/ml | CPM | S.D. | CPM | S.D. | CPM | S.D. |
| 10 | 2770 | 32.9 | 3860 | 11.5 | 98001 | 3.3 |
| 1 | 7421 | 11.6 | 11480 | 6.0 | 96002 | 1.9 |
| 0.1 | 26508 | 2.3 | 37794 | 2.3 | 100637 | 4.8 |
| 0.01 | 62536 | 5.3 | 75391 | 2.2 | 95146 | 0.8 |
| 0.001 | 77769 | 7.1 | 90660 | 9.3 | 96835 | 0.2 |
| 0.0001 | 85739 | 3.7 | 95597 | 10.6 | 81495 | 20.7 |
| 0.00001 | 90227 | 5.3 | 96132 | 6.2 | 94356 | 2.0 |
| 0.0 | 92748 | 6.5 | 95139 | 4.9 | 95203 | 6.5 |

(Standard deviation in %)

TABLE 3

Inhibition of human IgE synthesis

| | + 3 µg/ml Fc control | + 3 µg/ml huIL-4R/Fc |
|---|---|---|
| without IL-4 | < 6.9 | < 6.9 |
| + 3 ng/ml huIL-4 | 14.17 (2) | < 6.9 |
| + 30 ng/ml huIL-4 | 20.14 (8) | < 6.9 |

Human IgE data in ng/ml
In parentheses: percentage standard deviation

TABLE 4

Inhibition of the synthesis of allergen-specific IgE

100 SQ U/ml mite allergen Derm. Pt.

| Medium Control | Without Rec. | 3 µg/ml huIL-4R/Fc | 3 µg/ml Fc control |
|---|---|---|---|
| < 0.09 | 1.23 (4.1) | < 0.09 | 1.17 (5.6) |

Human IgE data in ng/ml
In parentheses: percentage standard deviation

TABLE 5

Mite-specific T-cell clones from the skin of a patient with atopic dermatitis

| | Autocrine IL-2 (U/ml, Bioassay) | Autocrine IL-4 (ng/ml, Bioassay) | Autocrine IL-4 (ng/ml, 3 µg/ml huIL-4R/Fc in Bioassay) | Proliferation |
|---|---|---|---|---|
| TH2 clone 1141 | | | | |
| 10 µg/ml ConA | < 25 | 49 (9) | < 1 | Inhibition |
| 10 µg/ml ConA + 3 µg/ml huIL-4R/Fc | < 25 | 10 (8) | < 1 | |
| TH1 clone 1150 | | | | |
| 10 µg/ml ConA | 97 (2) | 18 (29) | 8.8 (11) | No inhibition |
| 10 µg/ml ConA + 3 µg/ml huIL-4R/Fc | 88 (20) | 10 (5) | 6.3 (14) | |

(Standard deviation in %)

TABLE 6

Inhibition of the skin test reaction by muIL-4R

| Sensitization (pulmonary) | Treatment (i.p.) | Positive skin test to OVA | |
|---|---|---|---|
| PBS | — | 0/9 | 0 |
| OVA | — | 10/12 | 83.3 |
| OVA | muIL-4R | 2/9 | 22.2 |
| OVA | anti-IL-4 | 5/8 | 62.5 |

TABLE 7

Inhibition of antigen-specific IgE after tracheal constriction by muIL-4R

| Sensitization | OVA | OVA | PBS |
|---|---|---|---|
| Treatment | — | muIL-4R i.p. | — |
| Number of mice | 28 | 12 | 36 |
| Anti-OVA IgE | 2144 | 1126 | <20 |
| CV in % | 18.6 | 34.9 | |
| ES 50 | 2.47 | 3.4 | 4.18 |
| CV in % | 5.6 | 15.2 | 2.4 |

TABLE 8

Reduction in the number of animals with pulmonary sensitization and with a positive skin test by pulmonary administration of muIL-4R

| Sensitization | OVA | OVA | PBS |
|---|---|---|---|
| Treatment | — | muIL-4R inhaled | — |
| Number of mice | 28 | 8 | 36 |
| Anti-OVA IgE | 2144 | — | <20 |
| CV in % | 18.6 | | |
| ES 50 | 2.47 | 3.14 | 4.18 |
| CV in % | 5.6 | 24.8 | 2.4 |

TABLE 9

Effect of interleukin-4 receptor on induced chronic graft versus host disease (cGvHD)
Fraction of surviving animals

| Days after induction of cGvHD | Control animals | IL-4R treatment (2 mg/kg, 5 × i.v., days 27–31) | |
|---|---|---|---|
| | | huIL-4R/Fc | muIL-4R/Fc |
| 70 | 10/10 (100%) | 10/10 (100%) | 10/10 (100%) |
| 73 | 10/10 (100%) | 9/10 (90%) | 10/10 (100%) |
| 74 | 9/10 (90%) | 9/10 (90%) | 10/10 (100%) |
| 76 | 9/10 (90%) | 7/10 (70%) | 10/10 (100%) |
| 77 | 8/10 (80%) | 7/10 (70%) | 10/10 (100%) |
| 79 | 7/10 (70%) | 7/10 (70%) | 10/10 (100%) |
| 81 | 7/10 (70%) | 6/10 (60%) | 10/10 (100%) |
| 82 | 7/10 (70%) | 5/10 (50%) | 10/10 (100%) |
| 84 | 6/10 (60%) | 5/10 (50%) | 9/10 (90%) |
| 85 | 6/10 (60%) | 5/10 (50%) | 8/10 (80%) |
| 86 | 4/10 (40%) | 5/10 (50%) | 8/10 (80%) |
| 87 | 3/10 (30%) | 3/10 (30%) | 8/10 (80%) |
| 88 | 3/10 (30%) | 3/10 (30%) | 8/10 (80%) |
| 89 | 3/10 (30%) | 2/10 (20%) | 8/10 (80%) |
| 91 | 2/10 (20%) | 1/10 (10%) | 8/10 (80%) |
| 92 | 0/10 (0%) | 0/10 (0%) | 7/10 (70%) |
| 94 | — | — | 7/10 (70%) |
| 101 | — | — | 6/10 (60%) |
| 110 | — | — | 6/10 (60%) |

TABLE 10

Effect of interleukin-4 receptor on induced chronic graft versus host disease (cGvHD)
Protein in the urine of animals with glomerulonephritis

| Days after induction of cGvHD | Control animals | IL-4R treatment (2 mg/kg, 5 × i.v., days 27–31) | |
|---|---|---|---|
| | | huIL-4R/Fc | muIL-4R/Fc |
| 25 | 13 ± 6 | 15 ± 16 | 16 ± 12 |
| 44 | 234 ± 92 | 243 ± 109 | 95 ± 43 |
| 58 | 286 ± 113 | 279 ± 134 | 162 ± 96 |
| 64 | 313 ± 143 | 326 ± 126 | 196 ± 147 |
| 79 | 366 ± 149 | 360 ± 193 | 213 ± 196 |
| 85 | 460 ± 126 | 450 ± 158 | 227 ± 186 |
| 91 | 500 ± 0 | 500 ± 0 | 233 ± 192 |
| 100 | — | — | 249 ± 193 |
| 110 | — | — | 258 ± 184 |

TABLE 11

Effect of interleukin-4 receptor on induced chronic graft versus host disease (cGvHD)
Fraction of surviving animals

| Days after induction of cGvHD | Control animals | Cytokine receptor treatment (2 mg/kg, 5 × i.v., days 63–67) | |
|---|---|---|---|
| | | huIL-4R/Fc | muIL-4R/Fc |
| 65 | 10/10 (100%) | 10/10 (100%) | 10/10 (100%) |
| 70 | 9/10 (90%) | 10/10 (100%) | 10/10 (100%) |
| 71 | 8/10 (80%) | 9/10 (90%) | 10/10 (100%) |
| 72 | 8/10 (80%) | 9/10 (90%) | 9/10 (90%) |
| 73 | 7/10 (70%) | 9/10 (90%) | 9/10 (90%) |
| 74 | 7/10 (70%) | 7/10 (70%) | 9/10 (90%) |
| 75 | 7/10 (70%) | 5/10 (50%) | 9/10 (90%) |
| 76 | 7/10 (70%) | 5/10 (50%) | 9/10 (90%) |
| 77 | 6/10 (60%) | 5/10 (50%) | 9/10 (90%) |
| 78 | 5/10 (50%) | 3/10 (30%) | 9/10 (90%) |
| 79 | 3/10 (30%) | 3/10 (30%) | 7/10 (70%) |
| 80 | 3/10 (30%) | 3/10 (30%) | 7/10 (70%) |
| 81 | 3/10 (30%) | 3/10 (30%) | 7/10 (70%) |
| 82 | 3/10 (30%) | 3/10 (30%) | 7/10 (70%) |
| 83 | 3/10 (30%) | 2/10 (20%) | 7/10 (70%) |
| 84 | 1/10 (10%) | 2/10 (20%) | 6/10 (60%) |
| 85 | 1/10 (10%) | 2/10 (20%) | 6/10 (60%) |
| 86 | 0/10 (0%) | 2/10 (20%) | 6/10 (60%) |
| 87 | — | 0/10 (0%) | 5/10 (50%) |
| 88 | — | — | 5/10 (50%) |
| 89 | — | — | 5/10 (50%) |
| 90 | — | — | 5/10 (50%) |

TABLE 12

Effect of interleukin-4 receptor on induced chronic graft versus host disease (cGvHD)
Protein in the urine of animals with glomerulonephritis

| Date after induction of cGvHD | Control animals | Cytokine receptor treatment (2 mg/kg, 5 × i.v., days 63–67) | |
|---|---|---|---|
| | | huIL-4R/Fc | muIL-4R/Fc |
| 0 | 9 ± 15 | 11 ± 16 | 6 ± 13 |
| 10 | 15 ± 16 | 24 ± 34 | 19 ± 32 |
| 50 | 210 ± 69 | 203 ± 76 | 218 ± 83 |
| 65 | 276 ± 99 | 283 ± 103 | 297 ± 107 |
| 77 | 460 ± 126 | 443 ± 138 | 306 ± 146 |
| 85 | 500 ± 0 | 500 ± 0 | 328 ± 139 |
| 90 | — | — | 389 ± 154 |

TABLE 13

Effect of interleukin-4 receptor on induced chronic graft versus host disease (cGvHD)
Determination of immunoglobulin E

| Serum sampling, days | muIL-4R | | huIL-4R | |
|---|---|---|---|---|
| 0 | 0.6 | (30.7) | 0.77 | (37.0) |
| 24 | 601.1 | (27.9) | 776.7 | (39.8) |
| 38 | 891.2 | (47.4) | 1136.7 | (38.9) |
| 45 | 574 | (43.2) | 1176.3 | (9.4) |
| 52 | 302.56 | (33.0) | 1188.9 | (17.6) |
| 59 | 243.4 | (9.7) | 466 | (23.3) |
| 80 | 187.7 | (21.4) | 241.9 | (10.8) |

The IgE concentration data are in μg/ml of serum (averages of three animals, % standard deviations in parentheses)

TABLE 14

Treatment of a spontaneous autoimmune disease in MRL/1 mice similar to human systemic lupus erythematosus
Changes in survival rates

| Age of animals (weeks) | Untreated control MRL/1 mice | Buffer control MRL/1 mice | huIL-4R/Fc | muIL-4R/Fc |
|---|---|---|---|---|
| 15 | 10/10 (100%) | 10/10 (100%) | 11/11 (100%) | 11/11 (100%) |
| 16 | 10/10 (100%) | 10/10 (100%) | 11/11 (100%) | 11/11 (100%) |
| 17 | 10/10 (100%) | 10/10 (100%) | 10/11 (91%) | 11/11 (100%) |
| 18 | 9/10 (90%) | 10/10 (100%) | 10/11 (91%) | 11/11 (100%) |
| 19 | 8/10 (80%) | 8/10 (80%) | 9/11 (82%) | 11/11 (100%) |
| 20 | 7/10 (70%) | 8/10 (80%) | 8/11 (73%) | 11/11 (100%) |
| 21 | 6/10 (60%) | 7/10 (70%) | 8/11 (73%) | 10/11 (91%) |
| 22 | 6/10 (60%) | 6/10 (60%) | 6/11 (55%) | 9/11 (82%) |
| 23 | 5/10 (50%) | 5/10 (50%) | 6/11 (55%) | 8/11 (73%) |
| 24 | 5/10 (50%) | 4/10 (40%) | 5/11 (46%) | 7/11 (64%) |
| 25 | 4/10 (40%) | 4/10 (40%) | 4/11 (36%) | 7/11 (64%) |

TABLE 15

Treatment of a spontaneous autoimmune disease in MRL/1 mice similar to human systemic lupus erythematosus

| Age of animals (weeks) | Untreated control MRL/1 mice | Buffer control MRL/1 mice | huIL-4R/Fc | muIL-4R/Fc |
|---|---|---|---|---|
| Survival rate | 40 (4/10) | 40 (4/10) | 36 (4/11) | 64 (7/11) |
| Weight of lymph nodes (mg) | 2758 ± 1218 | 2819 ± 953 | 2881 ± 1028 | 1537 ± 882 |
| Weight of spleens (mg) | 646 ± 215 | 686 ± 224 | 659 ± 191 | 332 ± 153 |
| Proteinuria (mg/dl) | 338 ± 83 | 376 ± 39 | 378 ± 53 | 214 ± 40 |
| Leukocyte count (×10³/μl) | 18.6 ± 4.4 | 18.4 ± 5.0 | 18.7 ± 4.3 | 14.1 ± 4.6 |
| IgM RF (recip. titer) | 296 ± 85 | 311 ± 58 | 309 ± 66 | 225 ± 62 |
| dsDNA antibodies (recip. titer) | 1502 ± 231 | 1589 ± 334 | 1557 ± 258 | 1205 ± 262 |

TABLE 16

Treatment of an infection with Cysticercus (Taenia) crassiceps in mice with murine interleukin-4 receptor

| Treatment with | Body weight (gram) | Parasite burden (gram wet weight per single animal) | Parasite burden (gram wet weight per group) |
|---|---|---|---|
| muIL-4R | 35.7 | neg | neg |
| | | 0.1 | neg |
| | | 6.0 | 7.5 | 13.7 |
| | | neg | 0.1 |
| | | neg | neg |
| huIL-4R | 35.9 | < 0.1 | neg |
| | | < 0.1 | neg |
| | | 8.4 | 6.3 | 34.9 |

TABLE 16-continued

Treatment of an infection with Cysticercus (Taenia) crassiceps in mice with murine interleukin-4 receptor

| Treatment with | Body weight (gram) | Parasite burden (gram wet weight per single animal) | Parasite burden (gram wet weight per group) |
|---|---|---|---|
| | | 8.2 | 5.7 |
| | | 1.3 | 5.0 |
| Infection control | 35.8 | 1.0 | 5.8 |
| | | neg | 3.7 |
| | | 2.7 | 2.1 | 31.6 |
| | | 7.2 | 6.2 |
| | | 1.0 | 1.9 |
| 0 control | 34.5 | — | — |

What is claimed is:

1. A method for reducing the proliferation of T-helper cells of the TH2 type in a host having a condition wherein there is an increase of T-helper cells of the TH2 type comprising administering an effective amount of IL-4 receptor (IL-4R) of the same species as the host or a pharmaceutically active derivative thereof, to the host having said condition to reduce proliferation of T-helper cells of the TH2 type, wherein said condition is a Candida or Aspergillus infection.

2. The method of claim 1, wherein the Candida is *Candida albicans*.

3. A method for reducing the proliferation of T-helper cells of the TH2 type in a host having a condition wherein there is an increase of T-helper cells of the TH2 type comprising administering an effective amount of IL-4 receptor (IL-4R) of the same species as the host or a pharmaceutically active derivative thereof, to the host having said condition to reduce proliferation of T-helper cells of the TH2 type, wherein said condition is a Leishmania, Trichurida, Trichinella, Taenia, or Heligmosomoides polygyrus infection.

4. A method for reducing the proliferation of T-helper cells of the TH2 type in a host having a condition wherein there is an increase of T-helper cells of the TH2 type comprising administering an effective amount of IL-4 receptor (IL-4R) of the same species as the host or a pharmaceutically active derivative thereof, to the host having said condition to reduce proliferation of T-helper cells of the TH2 type, wherein said condition is a human immunodeficiency virus (HIV) infection.

5. A method for reducing the proliferation of T-helper cells of the TH2 type in a host having a condition wherein there is an increase of T-helper cells of the TH2 type comprising administering an effective amount of IL-4 receptor (IL-4R) of the same species as the host or a pharmaceutically active derivative thereof, to the host having said condition to reduce proliferation of T-helper cells of the TH2 type, wherein said condition is eosinophilia, vernal conjunctivitis, or systemic lupus erythematosus (SLE).

6. The method according to claim 1, 2, 3, 4, or 5, wherein the IL-4 receptor or a pharmaceutically active derivative thereof is a constituent of a fusion protein.

7. The method according to claim 6, wherein the fusion protein contains the IL-4 receptor or a pharmaceutically active derivative thereof and the Fc portion of an antibody.

8. The method according to claim 1, 2, 3, 4, or 5, wherein IL-4R or a pharmaceutically active derivative thereof is used in a combination product.

9. The method according to claim 8, wherein the combination product contains gamma-interferon.

10. The method according to claim 8, wherein the combination product contains one or more substances which inhibit the interaction of the cellular surface protein CD40 ligand with the cellular surface protein CD40.

11. The method according to claim 10, wherein at least one of the substances is a soluble determinant of the CD40 surface molecule or CD40/lg fusion protein.

12. The method according to claim 1, 2, 3, 4, or 5, wherein the method comprises intradermal, subcutaneous, dermal, nasal or pulmonary administration of IL-4R or a pharmaceutically active derivative thereof.

13. The method according to claim 12, wherein the method is a dermal administration of the IL-4R or pharmaceutically active derivative thereof.

14. The method according to claim 1, 2, 3, 4, or 5, wherein the IL-4R derivative is the extracellular region of human IL-4R.

15. The method according to claim 1, 2, 3, 4, or 5, wherein the host is a human.

* * * * *